United States Patent [19]

Avidan et al.

[11] Patent Number: 5,060,719
[45] Date of Patent: Oct. 29, 1991

[54] USING FLUIDIZED PARTICLES

[75] Inventors: Amos A. Avidan, Yardley, Pa.; Reuel Shinnar, Great Neck, N.Y.

[73] Assignee: Mobil Oil Corporation, Fairfax, Va.

[21] Appl. No.: 443,686

[22] Filed: Nov. 30, 1989

Related U.S. Application Data

[62] Division of Ser. No. 284,627, Dec. 15, 1988, Pat. No. 4,914,255.

[51] Int. Cl.⁵ .................................................. F28C 3/12
[52] U.S. Cl. ............................. 165/104.13; 165/104.16
[58] Field of Search ........................ 165/104.16, 104.13

[56]        References Cited
       U.S. PATENT DOCUMENTS

| | | | |
|---|---|---|---|
| 2,690,051 | 9/1954 | Peskin | 165/104.16 |
| 2,842,102 | 7/1958 | Blaskowsbi | 122/4 D |
| 2,934,551 | 4/1960 | Stringer | 165/104.16 |
| 3,756,942 | 9/1973 | Cattanach | 208/137 |
| 3,759,821 | 9/1973 | Brennan et al. | 208/93 |
| 3,760,024 | 9/1973 | Cattanach | 260/673 |
| 3,991,816 | 11/1976 | Klaren | 165/1 |
| 4,176,710 | 12/1979 | Gansauge et al. | 165/104 F |
| 4,403,650 | 9/1983 | Klaren | 165/104.16 |
| 4,513,160 | 4/1985 | Avidan et al. | 585/640 |

OTHER PUBLICATIONS

"Fluidized-bed Heat Exchanger Avoids Fouling Problems", Chemical Engineering, Feb. 15, 1988, p. 43.

Primary Examiner—Albert W. Davis, Jr.
Attorney, Agent, or Firm—Alexander J. McKillop; Charles J. Speciale; Robert B. Furr, Jr.

[57]            ABSTRACT

A method is disclosed for increasing heat transfer efficiency between a conduit and a gas flowing through the conduit by fluidizing in the gas stream a Geldart Type A powder having controlled fines content. The invention further provides a method for integrating two fluid beds to transfer heat from a heat source to a fluid-bed reaction zone.

11 Claims, 5 Drawing Sheets

USING FLUIDIZED PARTICLES

This is a divisional of copending application Ser. No. 284,627, file on Dec. 15, 1988, now U.S. Pat. No. 4,914,255 granted Apr. 3, 1990.

FIELD OF THE INVENTION

This invention provides a method for increasing the efficiency of heat transfer between a conduit and a gas flowing through the conduit. More particularly, the invention provides a method and apparatus for increasing the heat transfer coefficient between heat exchanger tubes and a gas flowing through the tubes of the heat exchanger. The present invention further provides a method for integrating two fluid beds to transfer heat from a heat source to a fluid-bed reaction zone.

BACKGROUND OF THE INVENTION

The use of suspended particles to enhance indirect heat transfer between fluids is taught, for example, in U.S. Pat. No. 2,690,591 to Peskin, issued Sept. 29, 1954. Peskin describes the use of suspended particles to increase heat transfer efficiency in closed cycle thermodynamic systems.

U.S. Pat. No. 3,991,816 to Klaren, issued Nov. 16, 1976, teaches a method and apparatus for exchanging heat between a moving fluid and a moving secondary fluid comprising passing a plurality of streams of secondary fluid upward through the moving primary fluid. Solids are suspended in the secondary fluid.

U.S. Pat. No. 4,176,710 to Gansauge et al. discloses a fluidized-bed reactor containing at least one vertical transfer tube for conveying a heat transfer fluid through the fluidized bed.

U.S. Pat. No. 4,403,650 to Klaren, issued Sept. 13, 1983, discloses a vertical shell and tube heat exchanger in which solid particles flow from a lower chamber to an upper chamber through the heat exchanger tubes and are returned to the lower chamber via a valved conduit.

The article "Fluidized-bed heat exchanger avoids fouling problems" Vol. 94, CHEMICAL ENGINEERING 43 (Feb. 15, 1988) discloses the use of finely divided particles to minimize heat exchanger tube fouling.

Transferring heat to a fluidized-bed reaction zone poses a particularly perplexing engineering problem. The most economically advantageous hydrocarbon conversion reactions carried out in such an environment include dehydrogenation and aromatization, both generally endothermic and both requiring high temperatures for acceptable yields. Aromatization of $C_3$-$C_8$ paraffins over a zeolite catalyst having the structure of ZSM-5, for example, requires a heat input of 350-1500 BTU per pound of feed at a reaction temperature of about 450° C. to 700° C. (824° F. to 1292° F.). The limitations of previously known heat transfer techniques have impeded the commercial development of such high temperature fluidized-bed conversion processes. Methods known in the art to transfer heat to the fluidized-bed reaction zone included preheating the catalyst or positioning a heat exchanger in the fluidized catalyst bed. Preheating the catalyst separately to around 700° C. (1292° F.) undesirably accelerated catalyst deactivation. On the other hand, the heat transfer coefficient between circulating fluids and the inner walls of heat exchanger tubes was found to be too low for economic operation. Thus it can be seen that it would be highly desirable to increase the efficiency of heat transfer to such fluid-bed reaction zones.

SUMMARY OF THE INVENTION

The present invention first provides a method for increasing the heat transfer coefficient between a conduit and a gas stream flowing through the conduit.

It has been found that the heat transfer coefficient between a conduit and a gas stream flowing through the conduit may be markedly enhanced by fluidizing a Geldart Type A powder in the gas stream and controlling the fines content of the powder within a specified range. While not presented to limit the scope of the invention by theory, it is believed that the controlled fines content improves the hydrodynamics of the system preventing segregation and gas bubble formation.

The method of the present invention for increasing the heat transfer coefficient between a conduit and a gas stream flowing through the conduit comprises the steps of fluidizing a Geldart Type A powder in the gas stream and maintaining the fines content of the Geldart Type A powder at less than about 50 wt %.

Further, the invention provides an integrated system for transferring heat to a fluid-bed reaction zone. In the most preferred embodiment of this integrated system, fluidized finely divided particles are maintained in a fluid bed located within the tubes of a heat exchanger positioned inside the fluidized-bed reaction zone. Hot flue gas generated in a lower section of the exchanger transfers heat directly to the fluid bed located within the heat exchanger tubes which then indirectly heats the surrounding reaction zone as it flows upward through the exchanger tubes.

The integrated heat transfer system of the present invention provides a further benefit in addition to its improved heat transfer. The combustion zone located in the lower section of the exchanger can generate flue gas at high temperatures in excess of 1650° C. (3000° F.) depending on the charge rates of fuel and amount of excess air. Without the inclusion of fluidized particles in the rising flue gas streams, such temepratures would be required to transfer a sufficient amount of heat to the fluidized-bed reaction zone. Moreover, the hot flue gas entering a heat exchanger tube at 1650° C. (3000° F.) and cooling to around 760° C. (1400° F.), as would be the case without the use of fluidized particles, would impose severe stress on the exchanger tubes. The metal alloys and/or refractory insulation essential to such a design would at best add significantly to the capital cost of the commercial design and could, in the case of highly endothermic reactions, render the indirect heat transfer from hot flue gas an impractical design alternative.

The invention still further includes a method for transferring thermal energy to a fluidized-bed reaction zone comprising the steps of fluidizing a Geldart Type A powder in a first gas stream to form a fluidized heat transfer mixture, maintaining the fines content of the Geldart Type A powder at less than about 50%, fluidizing finely divided catalyst particles in a second gas stream having a sufficient flow rate to fluidize the finely divided catalyst particles in a sub-transport regime thus forming a fluidized-bed reaction zone, transferring thermal energy from an energy source to the fluidized heat transfer mixture, and indirectly transferring thermal energy from the fluidized heat transfer mixture to the fluidized-bed reaction zone.

In its apparatus aspects, the invention includes a reactor system comprising a reactor having inlet and outlet nozzles, a heat exchanger comprising a plurality of heat exchanger tubes positioned inside the reactor, a heat exchanger inlet pipe which extends through the wall of the reactor and is connected to the heat exchanger, a heat exchanger outlet pipe which extends through the wall of the reactor and is connected to the heat exchanger, and means for flowing a hot gas through the heat exchanger. The apparatus may further comprise perforate filters at the inlet and outlet of each heat exchanger tube to retain the finely divided solids within the tubes. The means for flowing a hot gas through the heat exchanger may comprise a combustion chamber for generating flue gas which is either internal or external to the reactor. In another embodiment, the means for flowing a hot gas through the heat exchanger that comprise a fluid catalytic cracking regenerator for generating hot flue gas, conduit connecting the regenerator and the heat exchanger inlet pipe, and a flow control valve positioned in the conduit for regulating the flow of flue gas through the heat exchanger.

DETAILED DESCRIPTION

Figure 1:
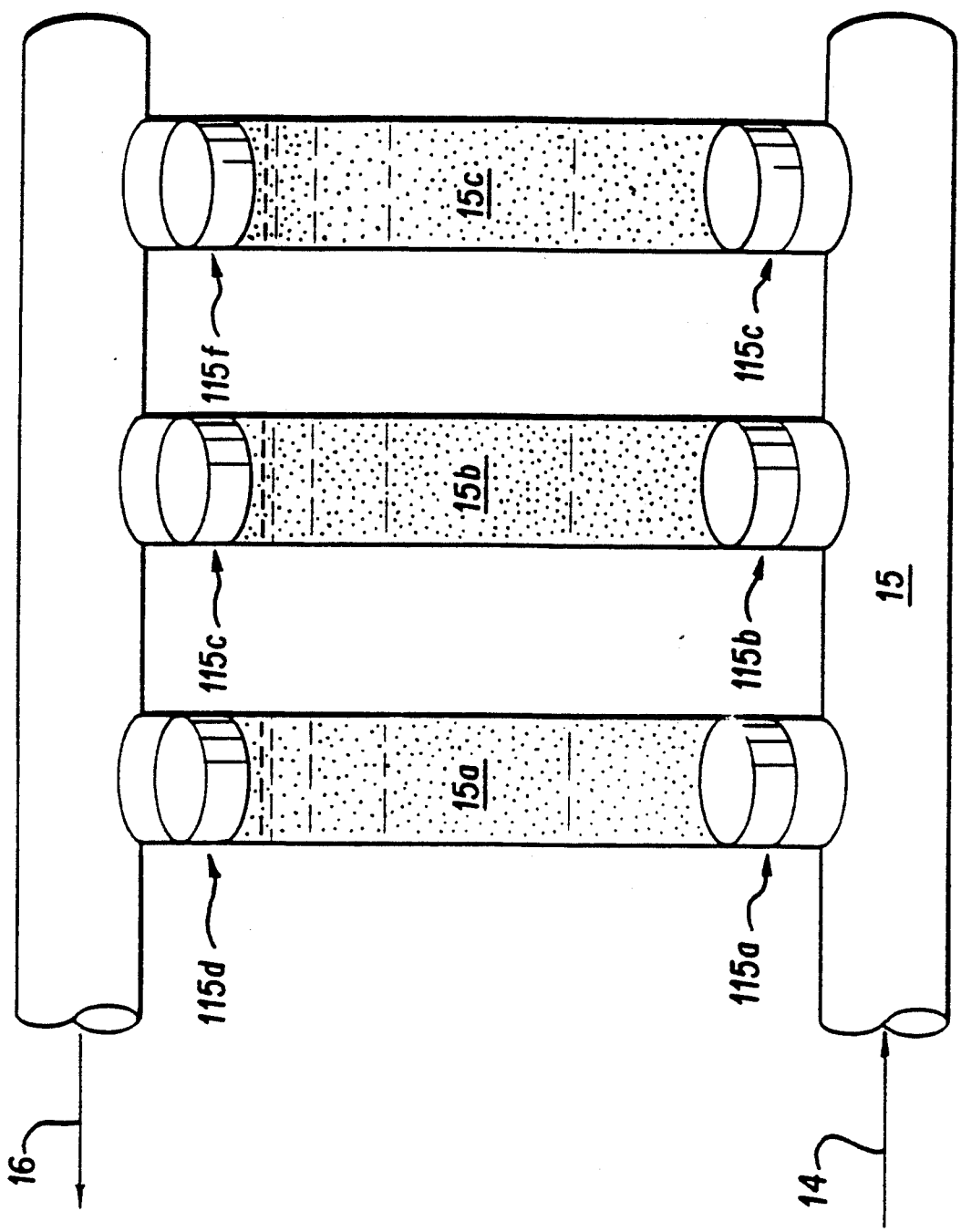
FIG. 1 is a simplified diagram showing a heat exchanger with filters at each end of the exchanger tubes to retain finely divided solid material within the tubes.

The method and apparatus of the present invention increase heat transfer efficiency to a fluidized-bed reaction zone. A method and apparatus are also disclosed for the conversion of aliphatic hydrocarbons to olefinic and/or aromatic hydrocarbons.

FLUIDIZED HEAT TRANSFER MIXTURE

The present invention increases the heat transfer coefficient between a conduit and a stream of gas flowing through the conduit by fluidizing a finely divided solid of controlled particle size distribution in the gas stream. In the most preferred embodiments, the fluidized mixture of gas and finally divided solids is restricted to remain within exchanger tubes.

The finely divided particles useful in the present invention generally have a major cross sectional dimension of less than 100 microns. The unexpected increase in heat transfer coefficient results, however, in controlling the particle size distribution, and in particular the relative concentration of fines. For the purpose of this disclosure, the term "fine" is defined as a particle having a major corss-sectional dimension of less than about 40 microns.

The beneficial effects of controlled particle size distribution are evident at fines concentrations ranging between 5 and 50 wt %. Preferably, fines concentration is maintained between about 10 and about 45 wt %, and more preferably between about 18 and 32 wt %. The most preferred operating mode comprises a fines concentration of about 25 wt %.

Spent FCC catalyst is particularly preferred for use in the present invention due to its relatively low cost and low rate of attrition. Materials useful in the present invention must remain relatively inert and resist attrition at temperatures up to 700° C. (1292° F.) and must be characterized by a combination of size, shape and density as to be classified as Geldart Type A powders. For a discussion of fluidization in the Geldart Type classification system see U.S. Pat. No. 4,513,160 to Avidan, as well as Geldart 7 Powder Technology 285 (1973), both of which are incorporated by reference as if set forth at length herein. Briefly, Geldart Type A powders are easily fluidizable finely divided solids.

CONVERSION PROCESSES

Hydrocarbon upgrading reactions compatible with the process of the present invention include the conversion of aliphatic hydrocarbons to olefinic and aromatic hydrocarbons. The following representative U.S. patents detail the feed compositions and process conditions for these reactions. Aromatization and dehydrogenation process conditions are summarized in Table 1.

U.S. Pat. No. 3,756,942, incorporated by reference as if set forth at length herein, discloses a process for the preparation of aromatic compounds in high yields which involves contacting a particular feed consisting essentially of mixtures of paraffins and/or olefins, and/or naphthenes with a crystalline aluminosilicate, e.g. ZSM-5, under conditions of temperature and space velocity such that a significant portion of the feed is converted directly into aromatic compounds.

U.S. Pat. No. 3,759,821, incorporated by reference as if set forth at length herein, discloses a process for upgrading catalytically cracked gasoline.

U.S. Pat. No. 3,760,024, incorporated by reference as if set forth at length herein, teaches a process for the preparation of aromatic compounds involving contacting a feed consisting essentially of $C_2$–$C_4$ paraffins and/or olefins with a crystalline aluminosilicate, e.g. ZSM-5.

Hydrocarbon feedstocks which can be converted according to the present process include various refinery streams including coker gasoline, light FCC gasoline, $C_5$–$C_7$ fractions of straight run naphthas and pyrolysis gasoline, as well as raffinates from a hydrocarbon mixture which has had aromatics removed by a solvent extraction treatment. Examples of such solvent extraction treatments are described on pages 706–709 of the *Kirk-Othmer Encyclopedia of Chemical Technology*, Third Edition, Vol. 9, John Wiley and Sons, 1980. A particular hydrocarbon feedstock derived from such a solvent extraction treatment is a Udex raffinate. The paraffinic hydrocarbon feedstock suitable for use in the present process may comprise at least 75 percent by weight, e.g. at least 85 percent by weight, of paraffins having from 5 to 10 carbon atoms.

The process and apparatus of the present invention is also useful in conjunction with thermal or catalytic dehydrogenation. A general discussion of thermal dehydrogenation is presented on pages 232–235 of the *Kirk-Othmer Encyclopedia of Chemical Technology*, Third Edition, Vol. 9, John Wiley & Sons 1980. Thermal dehydrogenation may be conducted in accordance with the present invention by charging a paraffinic feed stream to a fluidized bed of inert Geldhart Type A particles. Heat is transferred to the fluidized-bed reaction zone by means of a heat exchanger positioned inside the fluidized bed. Geldhart Type A particles having controlled fines content maximize the heat transfer coefficient between the hot gas flowing through the exchanger tubes and the reaction zone.

TABLE 1

| WHSV | Broad range: 0.1–300 hr$^{-1}$ |
| --- | --- |
| | Preferred range: 0.2–2 hr$^{-1}$ |
| OPERATING PRESSURE | Broad: 136–2170 kPa (5–300 psig) |
| | Preferred: 308–791 kPa (30–100 psia) |
| OPERATING TEMPERATURE | Broad: 450–820° C. (1000–1500° F.) |
| | Preferred: 560–620° C. (1050–1150° F.) |

CATALYSTS

The members of the class of zeolites useful herein have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing zeolite catalysts are particularly preferred for use in the present invention and are disclosed in U.S. Pat. No. 4,350,835 and U.S. Pat. No. 4,686,312, both of which are incorporated by reference as if set forth at length herein.

Zinc-containing zeolite catalysts are useful in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Paraffin dehydrogenation catalysts also include oxides and sulfides of Groups IVA, VA, VIA, VIIA and VIIIA and mixtures thereof on an inert support such as alumina or silica-alumina. Thus dehydrogenation may be promoted by sulfides and oxides of titanium, zirconium, vanadium, niobium, tantalum, chromium, molybdenum, tungsten and mixtures thereof. Oxides of chromium alone or in conjunction with other catalytically active species have been shown to be particularly useful in dehydrogenation. Other catalytically active compounds include sulfides and oxides of manganese, iron, cobalt, rhodium, iridium, nickel, palladium, platinum and mixtures thereof.

The above-listed metals of Groups IVA, VA, VIA, VIIA and VIIIA may also be exchanged onto zeolites to provide a zeolite catalyst having dehydrogenation activity. Platinum has been found to be particularly useful for promoting dehydrogenation over zeolite catalysts.

REACTOR HEAT EXCHANGER

FIG. 1 is a schematic representation of a heat exchanger in which the heat transfer coefficient between the tubes 15*a*, 15*b* and 15*c* and a gas flowing through the tubes is increased by fluidizing and retaining within the tubes a Geldart Type A powder having a controlled fines content.

A hot gas enters the lower section of exchanger 15 via conduit 14 and flows into tubes 15*a*, 15*b* and 15*c* through filters 115*a*, 115*b* and 115*c*, respectively. The filters may comprise screens, perforated sheets, sintered metal, or sintered ceramic but must permit the flow of gas without undue pressure drop while retaining within the tube essentially all of the finely divided powder.

The hot gas flows up through the tubes and transfers heat directly to the fluidized particles and is cooled as heat is transferred indirectly from the fluidized mixture of hot gas and finely divided particles through the tube walls. Filters 115*d*, 115*e* and 115*f* are positioned near the top of tubes 15*a*, 15*b* and 15*c*, respectively, and prevent entrained powder from escaping from the exchanger tubes. Cooled gas flows through the filters into an upper section of heat exchanger 15 and is withdrawn via heat exchanger outlet line 16.

FIRST EMBODIMENT

Figure 2:
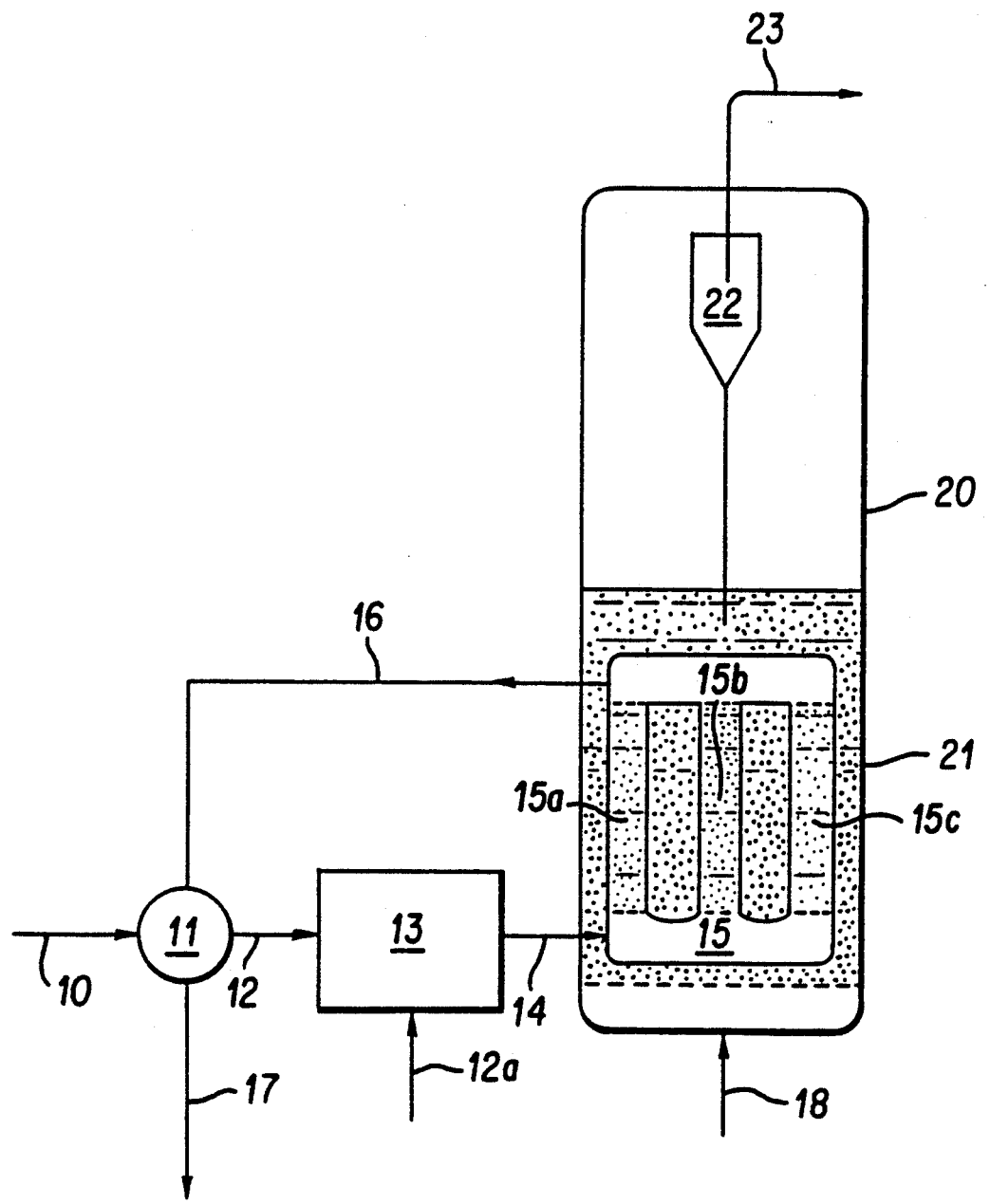
FIG. 2 is a simplified schematic diagram of a first embodiment of the reactor system of the present invention with an in-line combustion chamber located outside the reactor vessel.

In a first embodiment, the reaction zone is heated via a hot flue gas generated in an external on-line burner. Referring to FIG. 2, an oxygen-containing combustion gas, typically air, flows through line 10 to charge/effluent exchanger 11 where it is preheated by indirect exchange with heater effluent gas flowing through line 16. Preheated combustion gas is withdrawn from charge/effluent exchanger 11 through line 12 and charged to combustion zone 13 while cooled effluent gas is withdrawn from charge/effluent exchanger 11 through line 17. A controlled amount of fuel is charged to combustion zone 13 through line 12a and reacts with the combustion gas at elevated temperature to form a flue gas which is withdrawn from combustion zone 13 through line 14 and charged to exchanger 15 which is positioned in the lower section of reactor 20.

A hydrocarbon stream typically comprising $C_2$–$C_{10}$ aliphatic hydrocarbons is charged through conduit 15 to a bed of fluidized catalyst 21 in the lower section of reactor vessel 20. The catalyst bed is maintained at a temperature sufficient to vaporize the aliphatic hydrocarbon feed upon its entry into reactor vessel 20. Charge rate is maintained such that the volume of vaporized hydrocarbon will be sufficient to suspend the catalyst in a state of sub-transport fluidization.

Gaseous reaction products with entrained catalyst enter at least one cyclone separator 22. While only one cyclone is illustrated, it is to be understood that more than one cyclone may be used. Alternatively, one or more cyclones may be used in conjuction with a sintered metal filter positioned outside reactor 20 in conduit 16 to enhance separation of catalyst fines from the reaction products. Reaction products leave reactor 20 through conduit 23.

SECOND EMBODIMENT

In a second embodiment of the invention, hot flue gas is generated in a combustion zone located in a lower section of a heat exchanger positioned within the fluidized-bed reaction zone.

Figure 3:
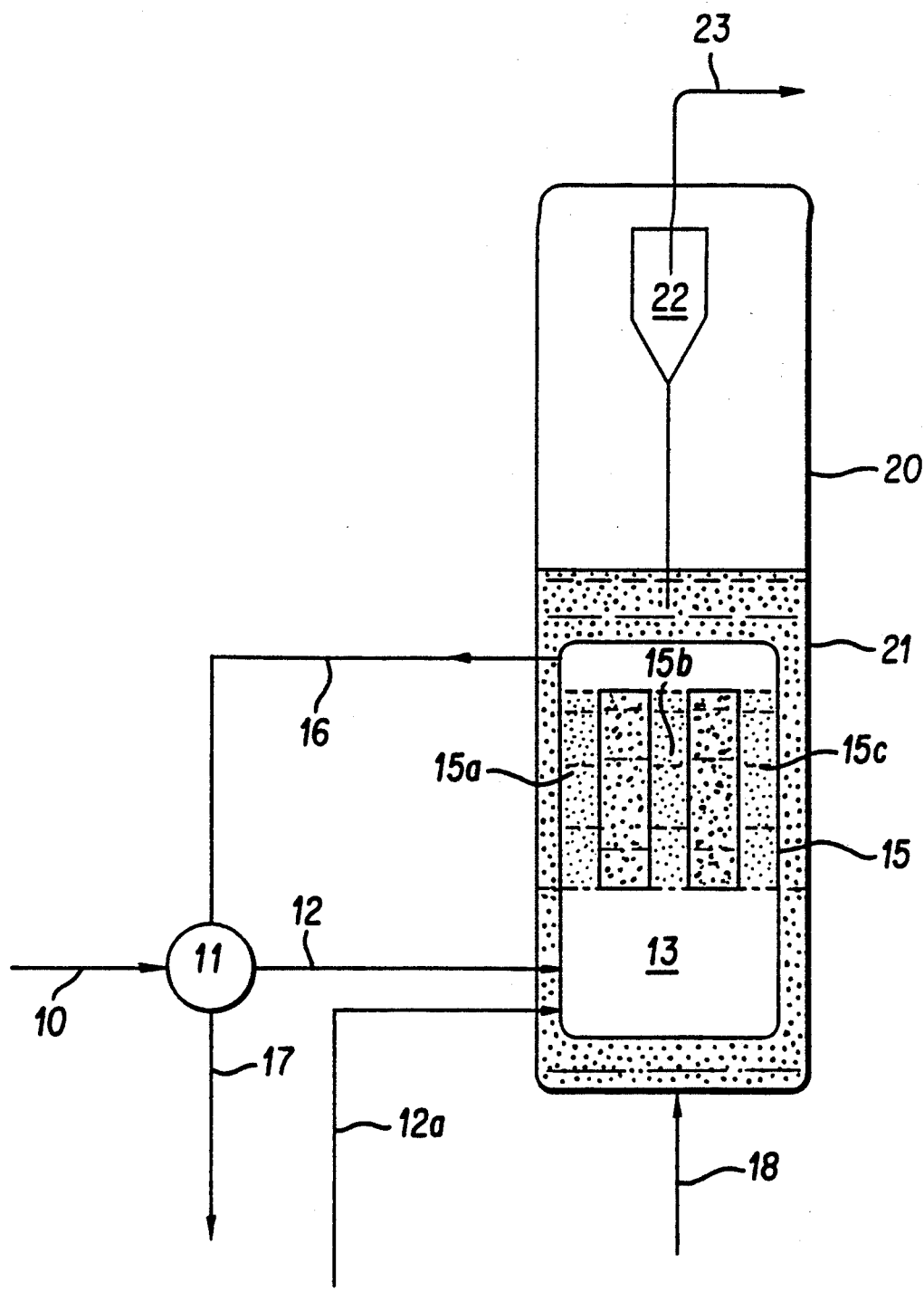
FIG. 3 is a simplified schematic diagram of a second embodiment of the reactor system of the present invention showing an in-line combustor located in a lower section of the reactor heat exchanger.

Referring now to FIG. 3, an oxygen-containing combustion gas, typically air, flows through line 10 to charge/effluent exchanger 11 where it is preheated as in the first embodiment. The preheated combustion gas is withdrawn from charge/effluent exchanger 11 through line 12 and charged to combustion zone 13 which is located in a lower section of heat exchanger 15. Fuel is charged directly to combustion chamber 13 through line 12a and reacts with the combustion gas to evolve a high temperature flue gas which flows upwardly through tubes 15a, 15b and 15c of heat exchanger 15. As described above, each of tubes 15a, 15b and 15c is equipped with filters on each end to retain within the tube a finely divided inert powder. Cooled flue gas is then withdrawn from heat exchanger 15 through line 16 and flows to charge/effluent exchanger 11.

THIRD EMBODIMENT

In a third embodiment of the present invention, heat is transferred from an FCC regenerator to the fluidized-bed reaction zone. Operating details of FCC units in general and FCC regenerators in particular can be found in: U.S. Pat. Nos. 2,383,636 to Wirth; 2,689,210 to Leffer; 3,338,821 to Moyer et al.; 3,812,029 to Snyder, Jr.; 4,093,537 to Gross et al; 4,118,338 to Gross et al. and 4,218,306 to Gross et al., as well as in Venuto et al. *Fluid Catalytic Cracking with Zeolite Catalysts*, Marcel Dekker, Inc., (1979). The entire contents of all the above patents and publications are incorporated herein by reference.

Figure 4:
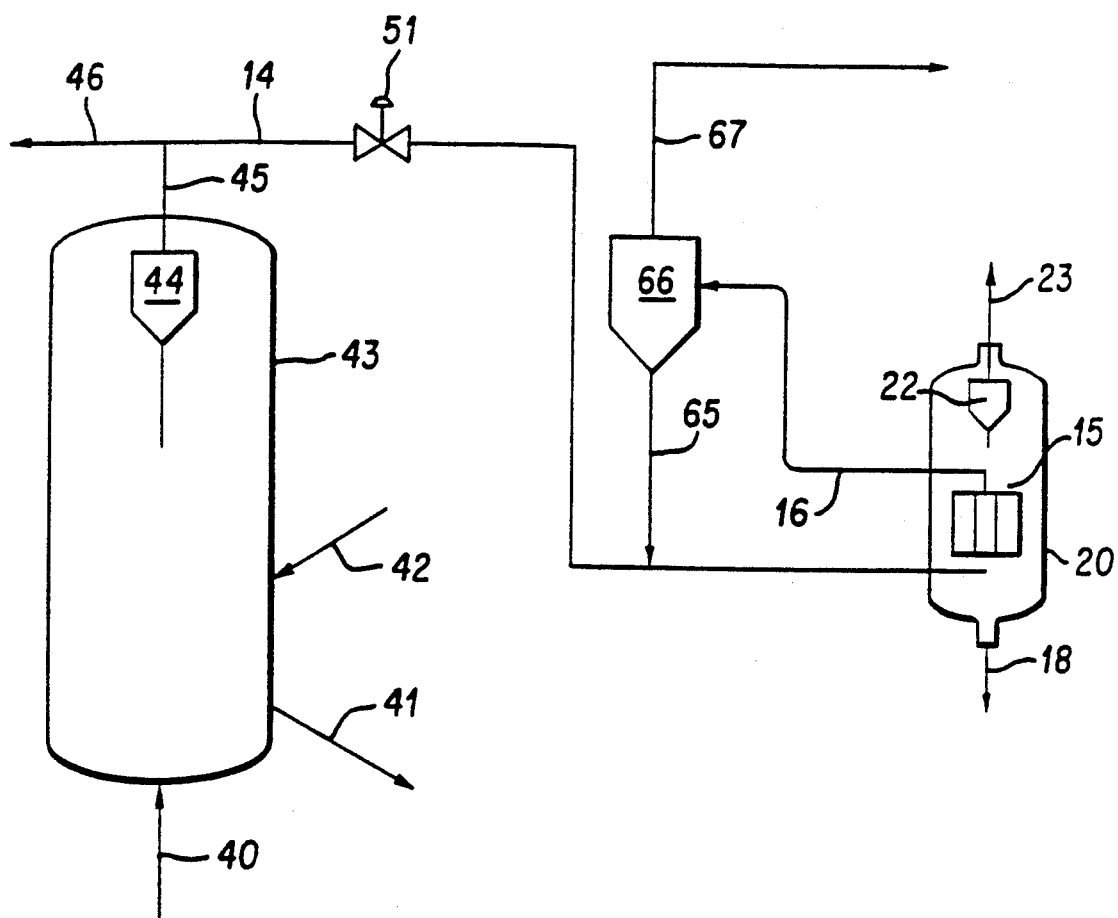
FIG. 4 is a simplified diagram of a third embodiment of the reactor system of the present invention in which flue gas from a fluidized cracking unit regenerator is mixed with recirculating finely divided solids to heat a reaction zone.

Referring to FIG. 4, deactivated cracking catalyst from an FCC reactor (not shown) flows through line 42 to regenerator vessel 43. Coke deposited on the deactivated catalyst burns in the presence of the oxygen-containing regeneration gas charged to regenerator 43 through line 40 yielding substantially inert flue gas and regenerated cracking catalyst. The regenerated cracking catalyst leaves vessel 43 through line 41 and returns to the FCC reactor riser (not shown). The flue gas together with catalyst fines rises through the regenerator vessel 43 and enters cyclone separator 44 in which flue gas and regenerated catalyst are separated. The flue gas flows out of vessel 43 through line 45 and is subsequently split between line 46 and line 14. Line 46 routes a portion of the flue gas to a heat recovery unit, e.g. steam generation. The balance of the flue gas flows through line 14 which is equipped with flow control value 51 and is joined by circulating solids flowing through line 65. The mixture of hot flue gas and fluidized solids flows through line 14 to heat exchanger 15 in reactor 20 as described above. However, in the fourth embodiment, the heat exchanger tubes are not equipped with filters to retain finely divided particles within the tubes. Finely divided particles circulate through a loop which includes exchanger 15, line 16, cyclone separator 66, line 65 and line 14. Operation of the fluidized-bed reactor is identical to that of the first three embodiments. The cooled fluidized mixture leaves heat exchanger 15 through line 14 and enters cyclone separator 66. Cooled flue gas flows out of cyclone separator 66 through line 67 and solid particles are recycled to the heat transfer loop through line 65 which feeds into line 10 downstream of control valve 51.

EXAMPLE 1—HEAT TRANSFER COEFFICIENT-COMPARATIVE

The first example shows a calculated heat transfer coefficient without fluidized particles to improve heat transfer.

A single tube multi-pass heat exchanger is positioned inside a two-foot inside diameter vessel. Heat transfer oil is passed through the tube which has an outside diameter of approximately two inches. Gas flowing through the vessel is maintained at pressures between about 250 and 400 kPa (22 and 43 psig) and temperatures between about 400° and 415° C. (752° and 779° F.). The heat exchange coefficient between the surface of the tube and the surrounding gas flowing through the vessel is calculated to be about 10 BTU/ft$^2$°F.

EXAMPLE 2—HEAT TRANSFER COEFFICIENT AS A FUNCTION OF FINES CONTENT

The second example illustrates the beneficial effects of fluidizing in a gas stream a Geldart Type A powder having controlled fines content.

Figure 5:
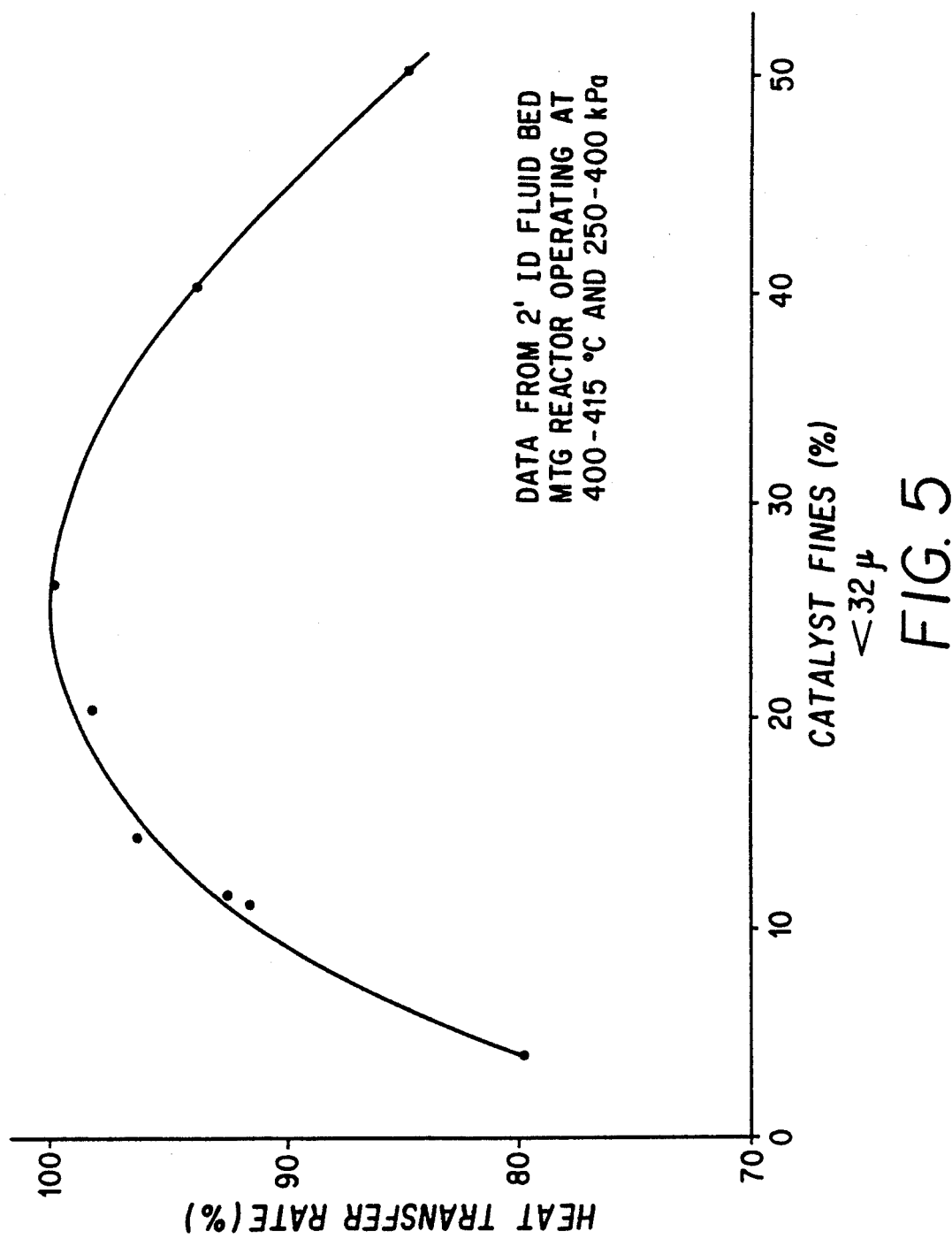
FIG. 5 is a graph of relative heat transfer rate as a function of fines loading in a two-foot inside diameter fluidized-bed reactor. Heat transfer was measured between the fluidized bed and a single oil-filled heat exchanger tube positioned inside the fluidized bed.

A single tube multi-pass heat exchanger was positioned in a two-foot inside diameter vessel as in the first example. Heat transfer oil was passed through the tube. A Geldart Type A powder was fluidized in a gas stream flowing through the vessel under pressures and temperatures of the first example. The weight percent fines (particles having a major cross-sectional dimension of less then 32 microns) was adjusted between about zero and about fifty weight percent. The maximum heat transfer coefficient of about 100 BTU/ft$^2°$F. was measured at approximately 25 wt % fines. Results are plotted in FIG. 5 which shows percent of maximum heat transfer coefficient as a function of weight % fines in the Geldart Type A powder.

EXAMPLE 3—FCC REGENERATOR

In the third example, hot flue gas from an FCC regenerator is mixed with spent FCC cracking catalyst to transfer the heat of reaction to the aromatization reactor.

A mixture of $C_2$–$C_4$ hydrocarbons is charged to the inlet of the aromatization reactor. The composition of the aliphatic charge stream is as follows:

| | |
|---|---|
| $C_1$ | 1 wt % |
| $C_2$ | 2 wt % |
| $C_2=$ | 2 wt % |
| $C_3$ | 19 wt % |
| $C_3=$ | 11 wt % |
| n-$C_4$ | 30 wt % |
| i-$C_4$ | 10 wt % |
| $C_4=$ | 25 wt % |
| | 100 wt % |

The fluidized-bed reaction zone is maintained at an average temperature of 565° C. (1049° F.) and a pressure of 170 kPa (10 psig). As a result, the aliphatic charge stream is vaporized upon its entry into the fluidized-bed reaction zone in the lower section of the aromatization reactor. Catalyst level in the reactor is selected to maintain a WHSV of about 1 hr$^{-1}$.

Hot flue gas is charged to the reactor heat exchanger where it contacts spent FCC cracking catalyst in accordance with the description of the fourth embodiment, above, to form a fluidized mixture retained within the reactor heat exchanger tubes comprising 25% by volume spent cracking catalyst. The FCC regenerator flue gas enters the heat exchange tubes positioned inside the aromatization reactor at a temperature of at least 700° C. (1292° F.).

The heat exchange tubes positioned inside the aromatization reactor are sized such that at least a 180° C. (270° F.) temperature differential is maintained between the fluidized mixture of inert gas and finely divided solid particles and the fluidized-bed reaction zone at the point where the heat exchange tubes enter the reaction zone.

The composition of the resulting product stream is as follows:

| | |
|---|---|
| $C_4-$ aliphatics | 36.8 wt % |
| $C_5+$ aliphatics | 0.1 wt % |
| $C_5+$ aromatics | 63.1 wt % |

Changes and modifications in the specifically described embodiments can be carried out without departing from the scope of the invention which is intended to be limited only by the scope of the appended claims.

What is claimed is:

1. A method for increasing the heat transfer coefficient between a conduit and a gas stream flowing through said conduit comprising the steps of:
   (a) fluidizing a Geldart Type A powder in said gas stream; and
   (b) maintaining the fines content of said Geldart Type A powder at from about 10 to about 45 weight percent.

2. The process of claim 1 wherein said fines content is between about 18 and about 32 weight percent.

3. The process of claim 1 wherein said fines content is about 25 weight percent.

4. A method for transferring thermal energy to a fluidized-bed reaction zone comprising the steps of:
   (a) fluidizing a Geldart Type A powder having a fines content of from about 10 to about 45 weight percent in a first gas stream to form a fluidized heat transfer mixture;
   (b) fluidizing finely divided catalyst particles in a second gas stream having a sufficient flow rate to fluidize said finely divided catalyst particles in a sub-transport regime thus forming a fluidized-bed reaction zone;
   (c) transferring thermal energy from an energy source to said fluidized heat transfer mixture; and
   (d) indirectly transferring thermal energy from said fluidized heat transfer mixture to said fluidized-bed reaction zone.

5. The process of claim 4 wherein said fines content is between about 18 and about 32 weight percent.

6. The process of claim 4 wherein said fines content is about 25 weight percent.

7. The process of claim 4 further comprising retaining said Geldart Type A powder within at least one heat exchanger tube positioned within said fluidized-bed reaction zone.

8. The process of claim 4 further comprising heating said heat transfer mixture by direct contact with combustion zone flue gas.

9. A method for transferring thermal energy to a fluidized-bed reaction zone comprising the steps of:
   (a) fluidizing a Geldart Type A powder in a first gas stream to form a fluidized heat transfer mixture containing from about 10 to about 45 weight percent fines wherein said fines have a major cross-sectional dimension of less than about 40 microns;
   (b) fluidizing finely divided catalyst particles in a second gas stream having a sufficient flow rate to fluidize said finely divided catalyst particles in a sub-transport regime thus forming a fluidized-bed reaction zone;
   (c) heating said fluidized heat transfer mixture of step (a) by directly contacting said fluidized heat transfer mixture with combustion zone flue gas;
   (d) indirectly transferring thermal energy from said fluidized heat transfer mixture to said fluidized-bed reaction zone.

10. The method of claim 9 wherein said fines content is from about 18 to about 32 weight percent.

11. The method of claim 9 wherein said fines content is about 25 weight percent.

* * * * *

UNITED STATES PATENT AND TRADEMARK OFFICE
CERTIFICATE OF CORRECTION

PATENT NO. : 5,060,719

DATED : October 29, 1991

INVENTOR(S) : Amos A. Avidan et al.

It is certified that error appears in the above-identified patent and that said Letters Patent is hereby corrected as shown below:

ON TITLE PAGE: Title  Insert -- HEAT TRANSFER -- before "USING FLUIDIZED PARTICLES".

Signed and Sealed this

Thirteenth Day of April, 1993

Attest:

STEPHEN G. KUNIN

Attesting Officer

Acting Commissioner of Patents and Trademarks